United States Patent
Focke et al.

[19]

[11] Patent Number: 6,158,193
[45] Date of Patent: Dec. 12, 2000

[54] METHOD AND APPARATUS FOR CHECKING (CIGARETTE) PACKS

[75] Inventors: Heinz Focke, Verden; Michael Czarnotta, Bremen, both of Germany

[73] Assignee: Focke & Co., (GmbH & Co.), Verden, Germany

[21] Appl. No.: 09/260,607

[22] Filed: Mar. 2, 1999

[30] Foreign Application Priority Data

Mar. 2, 1998 [DE] Germany ............................ 198 08 471
Sep. 2, 1998 [DE] Germany ............................ 198 39 852

[51] Int. Cl.$^7$ ..................................................... B65B 57/00
[52] U.S. Cl. ......................................... 53/53; 53/69; 53/76
[58] Field of Search ..................................... 53/53, 76, 75, 53/69, 67; 209/536, 535, 939, 934, 597, 576

[56] References Cited

U.S. PATENT DOCUMENTS

| | | | |
|---|---|---|---|
| 4,053,056 | 10/1977 | Day ........................................ | 53/53 X |
| 4,559,754 | 12/1985 | Bacon ................................... | 53/76 X |
| 4,858,770 | 8/1989 | Gamberini .............................. | 53/53 X |
| 5,412,926 | 5/1995 | Focke ..................................... | 53/53 X |
| 5,784,855 | 7/1998 | Focke et al. ............................. | 53/53 |

FOREIGN PATENT DOCUMENTS

| | | |
|---|---|---|
| 330 495 | 8/1989 | European Pat. Off. . |
| 523 441 | 1/1993 | European Pat. Off. . |
| 38 01 388 | 7/1988 | Germany . |
| 35 32 068 | 8/1989 | Germany . |
| 42 12 676 | 10/1992 | Germany . |
| 195 15 153 | 11/1996 | Germany . |
| 197 01 618 | 7/1998 | Germany . |

*Primary Examiner*—Eugene Kim
*Attorney, Agent, or Firm*—Sughrue, Mion, Zinn, Macpeak & Seas, PLLC

[57] ABSTRACT

For the purpose of checking packs (10), in particular cigarette packs, for the correct configuration of the outer appearance, the packs (10) are moved past stationary optoelectronic checking means, namely cameras (32, 33). The latter register outer surfaces of the packs (10). The checking means, namely cameras (32, 33), are triggered by the pack to be checked via an activating sensor (39). A downstream ejector (34) is actuated by a further sensor, namely by a defect sensor (42), which reacts to a defective pack.

16 Claims, 6 Drawing Sheets

:
METHOD AND APPARATUS FOR CHECKING (CIGARETTE) PACKS

BACKGROUND OF THE INVENTION

The invention relates to a method of checking packs, in particular cigarette packs, for the correct configuration of the outer appearance and for the purpose of separating out defective packs, it being the case that the packs are transported by a conveyor along a checking section and are moved past stationary checking means, in particular at least one camera, and defective packs are separated out downstream of the checking means. The invention also relates to an apparatus for implementing the method.

In the production of high-quality packs, in particular cigarette packs, the correct outer appearance of the (cigarette) packs should be ensured despite the high output of the packaging machines. For this purpose, it is known for the outer appearance of the finished packs to undergo a checking operation and for packs which have defective printing on them and/or are not of the correct configuration to be separated out.

For the purpose of checking the packs, the checking means used are preferably cameras, which record the outer image of the pack which is to be checked and compare this in an evaluation unit with the stored image of a correct pack. The evaluation unit actuates, as appropriate a (mechanical) ejector for any defective pack. The checking operation which the packs undergo takes place during the preferably continuous transportation of the packs.

SUMMARY OF THE INVENTION

The object of the invention is to ensure, during such a method of checking (cigarette) packs, that a precise image of the pack can be recorded despite a high conveying speed. In order to achieve this object, the method according to the invention is characterized in that the checking means, in particular the camera(s), can be activated cyclically for the purpose of registering in each case one pack moved past the checking means, and in that the checking means can be switched on by an activating sensor, which is activated by the pack which is to be checked.

Accordingly, in the case of the method according to the invention, it is ensured that the checking means, in particular cameras are activated or switched on exactly at the moment at which the pack assumes an optimum position in relation to the cameras or the like. At the same time, or as an alternative, it is also possible for a corresponding illumination means to be switched on, with the result that, despite the continuous, high conveying speed of the packs, a precise image of the same is recorded. The activating sensor is preferably a light barrier, through which the pack which is to be checked is moved.

A further special feature of the invention is the control of an ejector for the purpose of separating a defective pack out of the conveying stream. The ejector is actuated by the evaluation unit. Arranged upstream, in the conveying direction, of the ejector, however, is a defect sensor, in particular a light barrier, which has to be actuated if the ejector is to become active for the purpose of separating out the relevant pack. The defect sensor for the ejector works with an "evaluation window", that is to say with a conveying region of the packs, such that the ejector—once a defective pack has been established beforehand—only becomes active if the relevant pack appears in the evaluation window of the defect sensor within a certain period of time. If this requirement is not fulfilled, the invention provides for a plurality of successive packs, in particular three packs, to be separated out as a precaution.

The cameras, the sensors and the ejector are arranged in a specific manner and are controlled in dependence on the machine cycle.

BRIEF DESCRIPTION OF THE DRAWINGS

Further details of the invention are described hereinbelow with reference to exemplary embodiments of the apparatus. In the drawings.

DESCRIPTION OF PREFERRED EMBODIMENTS

The details which are illustrated in the drawings relate to the checking of cuboidal packs 10, namely cigarette packs. These packs come from a packaging machine or from a drying turret (not shown) assigned to the packaging machine. The packs 10 are introduced one after the other into a horizontal conveying section 11. In the region of the latter, the packs 10 undergo the checking operation during transportation.

Figure 1:
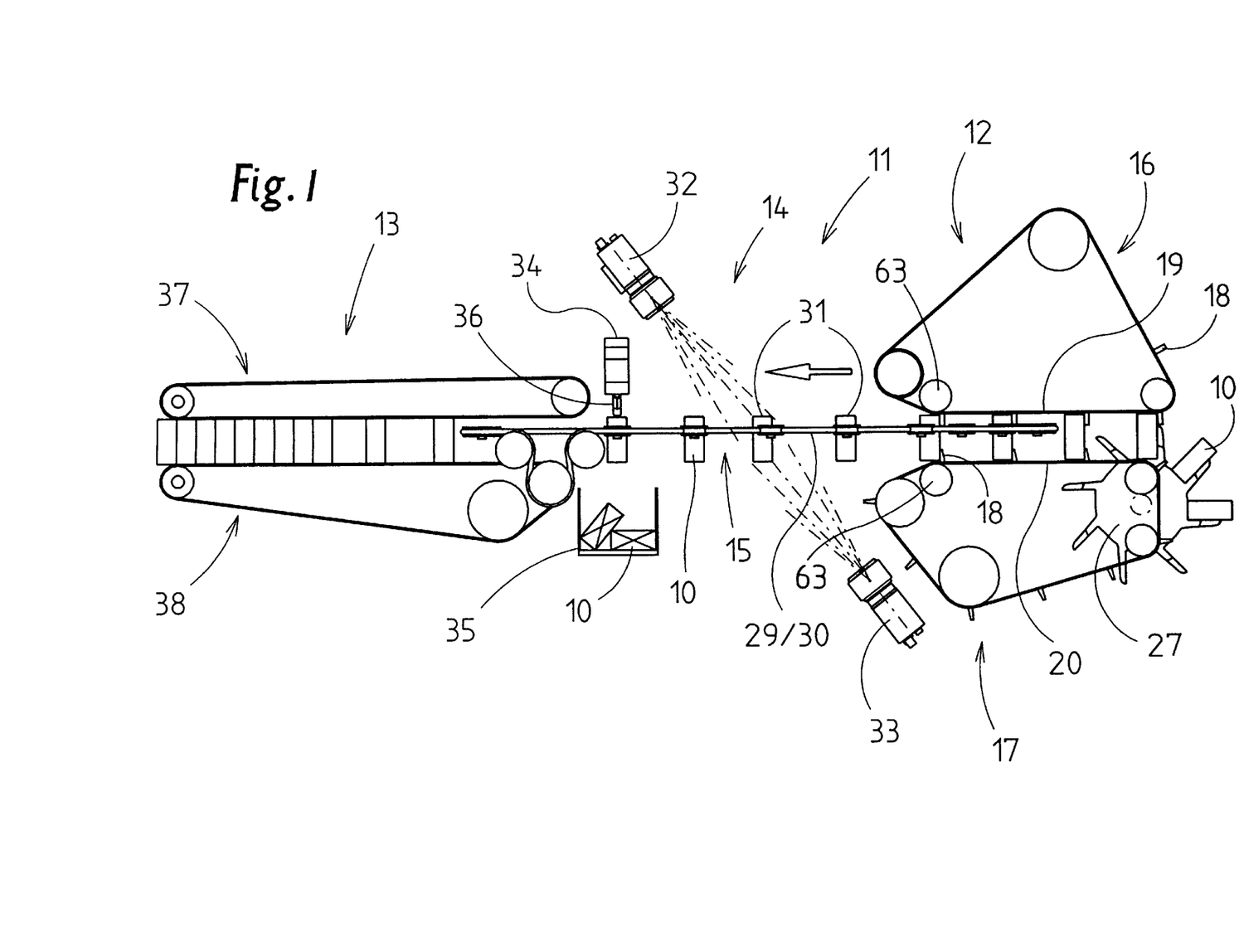
FIG. 1 shows a schematic side view of an apparatus for checking (cigarette) packs.

The conveying section 11 comprises a plurality of endless conveyors which receive, and pass on, the packs 10 one after the other. A checking section 14 is formed between a feed conveyor 12 and a removal conveyor 13. In the region of said checking section, packs 10 are transported by a checking conveyor 15.

The feed conveyor 12 comprises an endless, driven top belt 16 and a likewise driven, endless bottom belt 17. The top belt 16 and bottom belt 17 have carry-along elements 18 which each grip a pack 10 on the rear side, with the result that these packs 10 are conveyed at the same spacing apart from one another. In this case, the packs 10 are gripped between a conveying strand 19 of the top belt 16 and a conveying strand 20 of the bottom belt 17. The relative positioning of the packs is such that a large-surface-area front side 21 and a corresponding rear side 22 are oriented respectively forwards and rearwards in the conveying direction. Narrow, elongate side surfaces 23, 24 butt against the top and bottom conveying strands 19, 20. End surfaces 25, 26 are directed sideways.

With this relative positioning, the packs 10 are introduced into the region of the feed conveyor 12 by a preliminary conveyor, namely by a rotationally driven star wheel 27. The latter grips in each case one pack by way of approximately radially directed carry-along elements and introduces the pack between the conveying strands 19 and 20.

Figure 2:
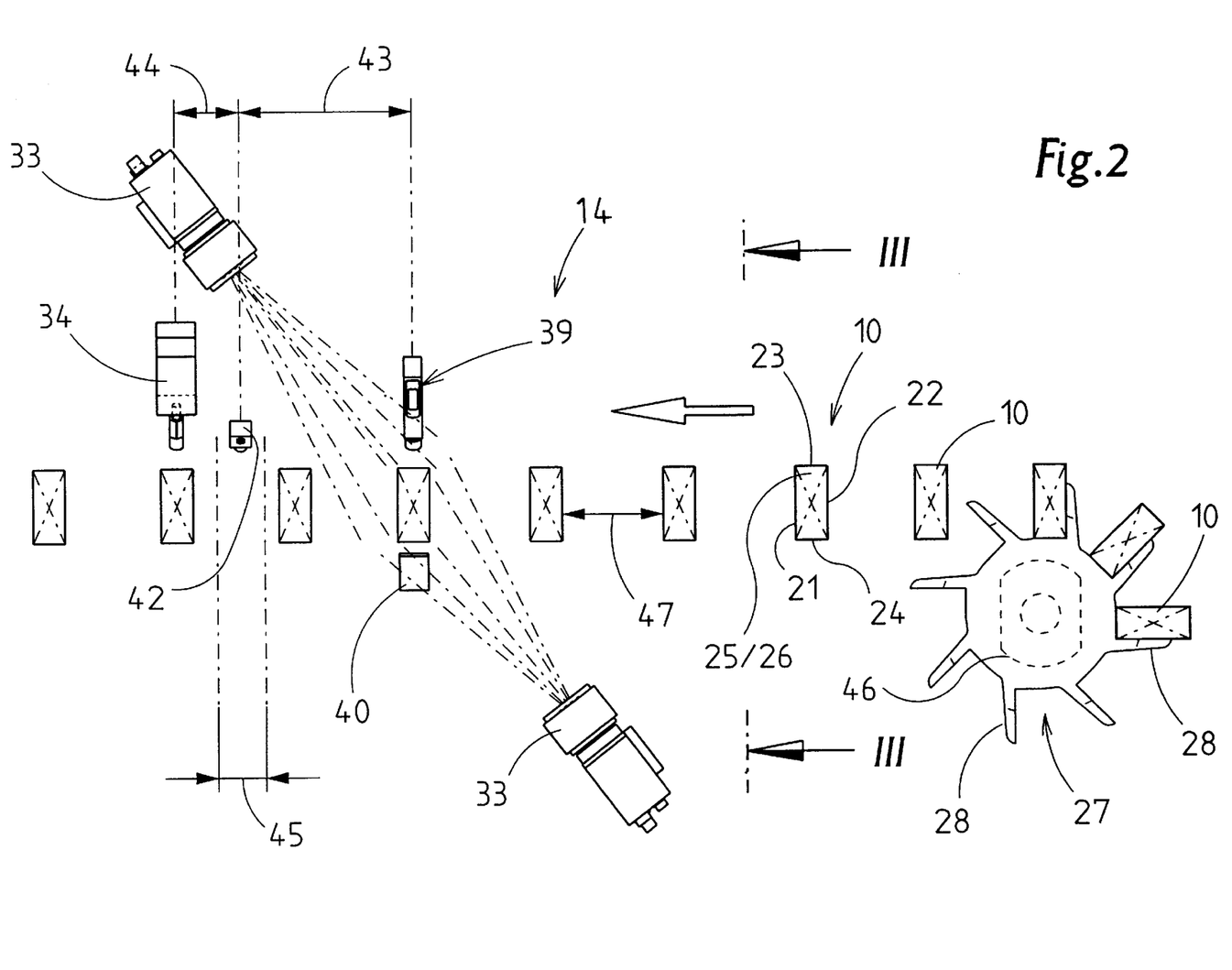
FIG. 2 shows an illustration of the apparatus according to FIG. 1 without conveying means.

The checking conveyor 15, which receives the packs 10 from the feed conveyor 12, exclusively comprises lateral, narrow belts, in particular endless round bands 29, 30. The latter have a conveying strand resting against mutually opposite, sideways-directed surfaces of the packs 10, namely the end surfaces 25 and 26. The relative positioning is selected such that the round bands 29, 30 butt against the packs 10 in a top cross-sectional region of the same. The round bands 29, 30 run over lateral supporting rollers 31.

Positioned in the region of the checking conveyor 15 are checking means for the purpose of registering the outer image of the packs 10 during transportation. In the present case, these means are cameras 32, 33 which are each positioned above and beneath the conveying section 11 and the checking conveyor 15, respectively. The cameras 32, 33 are arranged in an oblique position, to be precise such that each camera 32, 33 registers at least two surfaces of a pack 10, that is to say in the present case a front side 21 and a side surface 23 as well as a rear side 22 and a bottom side surface 24, respectively. The cameras 32, 33 register the outer appearance, that is to say in particular the printing or the presence of a revenue stamp, but also defects in configuration.

Defective packs 10 are separated out downstream of the checking means, in the region of the checking conveyor 15, to be precise by an ejector 34 which acts on the relevant pack 10 from above and discharges, or levers out, said pack downwards into a collecting container 35 from the position between the round bands 29, 30. The ejector 34 is provided with an extensible push rod 36 which is activated by a pressure medium.

The packs 10 of the correct design are transferred from the checking conveyor 15 to the removal conveyor 13. The latter comprises, in turn, a top conveying belt 37 and a bottom conveying belt 38. The correct packs 10 are transported away between these conveying belts 37 and 38 without the relative positions being changed.

The optoelectronic checking means for the packs 10, that is to say the cameras 32, 33, are not activated at all times; rather, they are only switched on briefly for the purpose of checking or sensing a pack 10 transported past them. The pack 10 which is to be checked itself triggers a signal for the purpose of activating the cameras 32, 33. For this purpose, the pack 10 is moved past a sensor, namely an activating sensor 39 positioned alongside the movement path of the packs 10. Said sensor is activated by the pack 10 which is to be checked. The activating sensor 39 produces a signal for the purpose of switching on or activating the cameras 32, 33 and, if appropriate, an illumination means.

Figure 3:
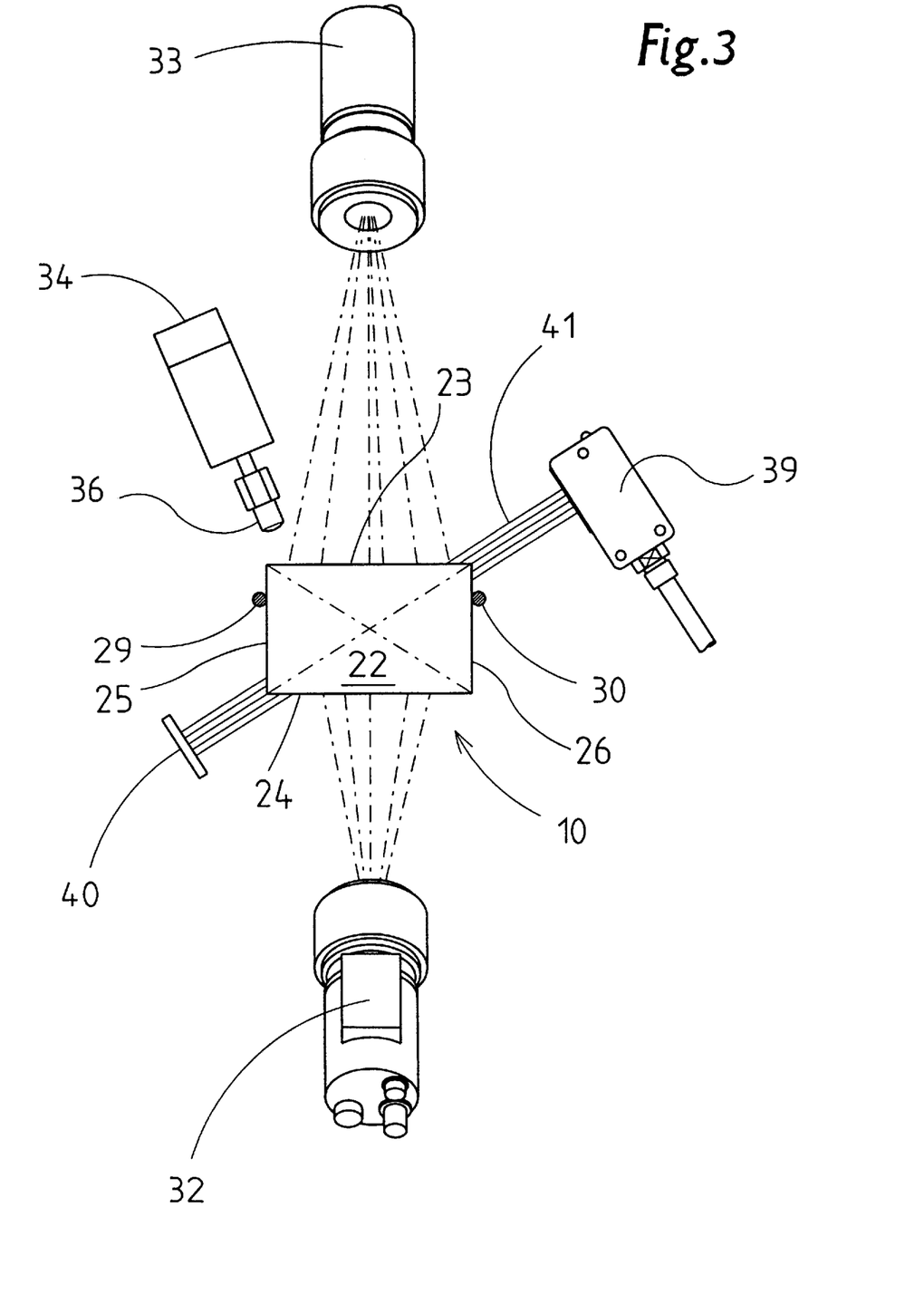
FIG. 3 shows, on an enlarged scale, a transverse view of the apparatus according to FIG. 2 in the section plane III—III of FIG. 2.

The activating sensor 39 works with a light barrier which is interrupted by the pack 10. For this purpose, the activating sensor 39 comprises a transmitter and receiver. A light beam emitted by the transmitter is reflected by a mirror 40 which is arranged on the opposite side of the movement path of the packs 10, and received by the receiver.

As can be seen from FIG. 3, the activating sensor 39 and mirror 40 are positioned in a specific manner relative to the movement path of the packs 10, that is to say such that the light beam 41 is oriented in the direction of a diagonal of the large-area surfaces, namely front side 21 and rear side 22, which are oriented in the conveying direction. In this case, the activating sensor 39 is arranged above the movement path and the mirror 40 is arranged beneath the same or vice versa. This positioning of the activating sensor 39 and the light beam 41 ensures that, even with any oblique or offset positioning of the packs 10, the cameras 32, 33 are made to operate when a region of the pack 10, possibly one which projects in the conveying direction, passes into the region of the light beam 41.

Alternatively, it is also possible for the transmitter and receiver of the activating sensor 39 to be arranged separately from one another. In this case, a mirror 40 can be dispensed with. Instead of the mirror 40, the receiver is then arranged opposite the transmitter arranged in the activating sensor 39.

A further special feature resides in the actuation of the ejector 34. The latter is likewise assigned a sensor, namely a defect sensor 42. The defect sensor 42 also works on the basis of a light barrier, the light being reflected by the pack 10 moved past it.

The defect sensor 42 is arranged between the activating sensor 39 and the ejector 34, to be precise at a predetermined spacing 44 from said ejector. Once a defective pack has been identified beforehand, the ejector 34 is made to operate by the defect sensor 42.

The interaction of the checking and separating-out means is such that the defect sensor 42 assumes a double function. The 40 defect sensor 42 is switched on at all times and thus monitors the packs 10 running past it, that is to say packs 10 of the correct design as well. In this case, the defect sensor 42 checks as to whether the packs 10 are transported at the predetermined spacing.

If the checking means, namely cameras 32, 33, establish a defective pack 10, the ejector 34 receives a corresponding actuating signal. As soon, then, as this defective pack 10 is conveyed past the defect sensor 42, the defect sensor 42 produces a signal for bringing the ejector 34 into operation. Said ejector becomes active—with a certain delay, which corresponds to the spacing 44 or, to take account of any possible idle times, for example of the ejector 34, is somewhat shorter—and discharges the pack 10 out of the region of the checking conveyor 15.

For the purpose of ensuring the functional sequences, there is a certain spacing 43 between the activating sensor 39 and the defect sensor 42. This spacing 43 determines the period of time which the defective pack 10, established if appropriate in the region of the activating sensor 39, requires, in the case of a certain (rotational) speed of the machine, in order to pass into the region of the defect sensor 42.

It is also possible—as is explained hereinbelow—for the spacing 43 to be expressed in an angle of rotation or cycle of the machine. A certain wheel of the machine, for example one connected to the drive, runs as reference wheel. It is coupled to the operating cycle or speed of the machine and has a defined diameter. It is thus possible, with reference to the angle of rotation of this wheel, to determine the advancement of a pack. It is likewise possible for the conveying speed of the machine to be determined from the rotational speed of the wheel. The spacing 43 thus determines not just a period of time but also a certain machine cycle or angle of rotation of the machine.

The defect sensor 42, in turn, has the ejector 34 arranged upstream of it at a likewise predetermined spacing 44. This provides the delay, upon actuation of the ejector 34, in order to ensure that the defective pack 10 is discharged once it has been detected by the defect sensor 42.

The defect sensor 42 works with an evaluation window 45. The latter forms a tolerance region for the incoming packs or the actuation of the ejector 34. The defect sensor 42 produces an actuating signal for the ejector 34 when a (defective) pack 10 appears in the region of the evaluation window 45, or, in temporal terms, in a corresponding time window. If in contrast—following a corresponding indication by the evaluation unit—a defective pack 10 is not detected within the evaluation window 45 following a predetermined period of time or path—corresponding to a predetermined angle of rotation or cycle of the machine—there is a risk that the packs 10 have not been transported at the correct spacing. In this case, as a precaution, a larger number of packs 10, preferably three successive packs 10, are separated out by the ejector 34. This is based on the assumption that the actually defective pack 10 is also reliably sensed and separated out in this way.

The functioning of the checking means and the ejector is controlled in dependence on the machine cycle. For this purpose, the star wheel 27 is assigned an angular encoder 46, which produces an exact signal corresponding to a means running along with the packaging machine, for example a conveying strand 19, 20 or a round band 29, 30, or in dependence on the current operating speed of the packaging machine and thus reproduces the current conveying speed of the packs 10 in the region of the conveying section 14. The star wheel 27 is connected to the drive of the packaging machine. The rotational speed corresponds to the operating speed of the packaging machine at all times.

The defect sensor 42 fulfills a double function and, for this purpose, is active at all times. On the one hand, as described, the ejector 34 is actuated at a precise time for the purpose of separating out a defective pack 10. On the other hand, however, the defect sensor 42 monitors at all times the correct transportation of the packs 10, that is to say in terms of the spacing 47 between the packs. The defect sensor 42 is set for the packs 10 being moved past it at certain spatial or temporal intervals, in accordance with the operating speed of the packaging machine or the distance predetermined by the angular encoder 46. If the spatial or temporal intervals—taking account of a tolerance region—are not observed, it is assumed that transportation of the packs 10 in the region of the conveying section 11 is proceeding incorrectly.

Figure 4:
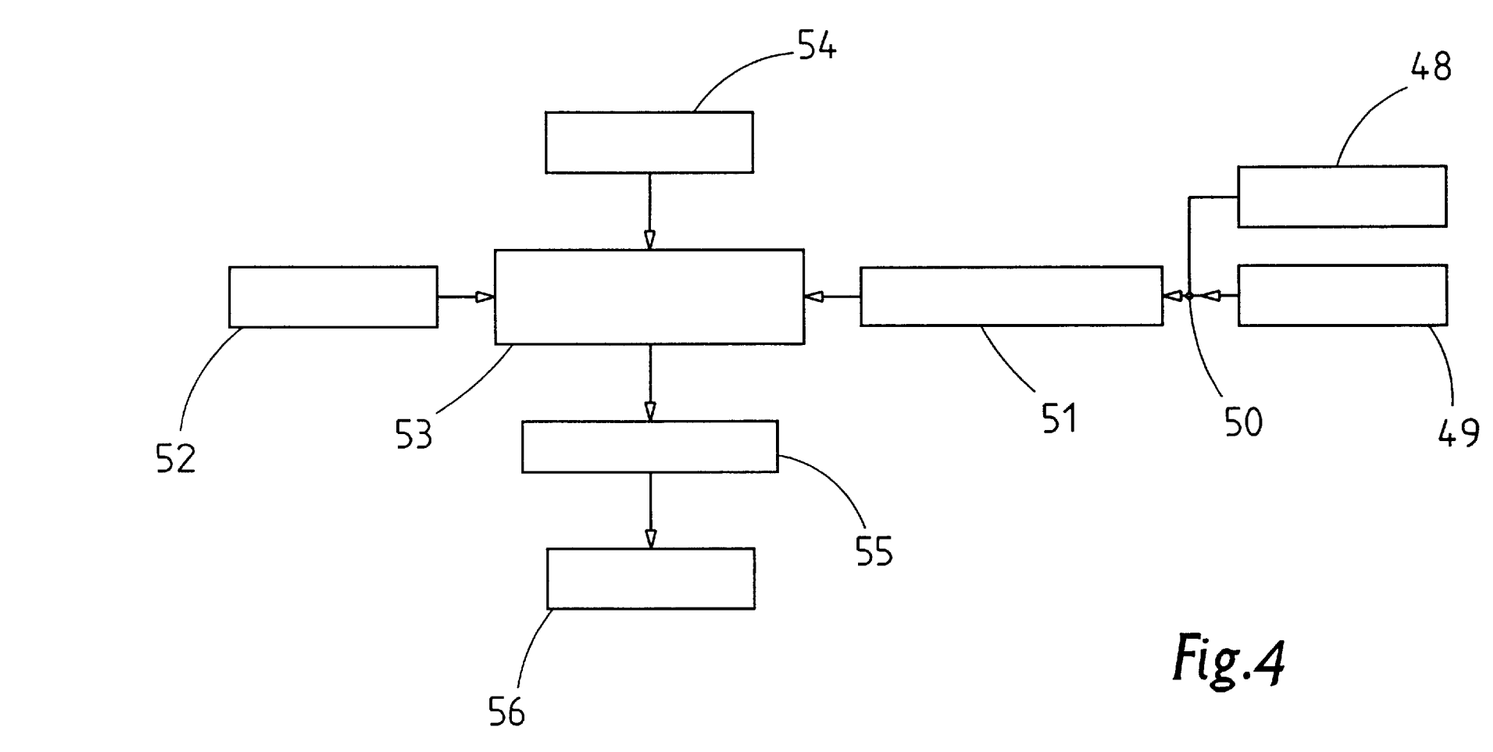
FIG. 4 shows a schematic illustration of the controls of an ejector.

FIG. 4 shows the control of the ejector 34. The angular encoder 46, in proportion to the operating speed of the packaging machine, supplies a measured value 48 of pulses per second. This measured value 48 is calculated with a set parameter of the reaction time 49 of the ejector 34 in milliseconds, to be precise by multiplication in the multiplier 50. Moreover, this product is then divided by a thousand to obtain a correction value 51. This correction value 51 is subtracted from a set parameter 52 which represents the distance between the ejector 34 and the defect sensor 42. This subtraction 53 is brought about by a signal 54 of the defect sensor 42. The difference calculated in this way gives the number of angular-encoder pulses which have to pass before the ejector 34 is activated. Once this period of time has passed, a signal 55 is produced for the purpose of actuating the ejector. Following a brief idle time or, if appropriate, even simultaneously, the ejection 56 of a cigarette pack takes place.

Figure 5:
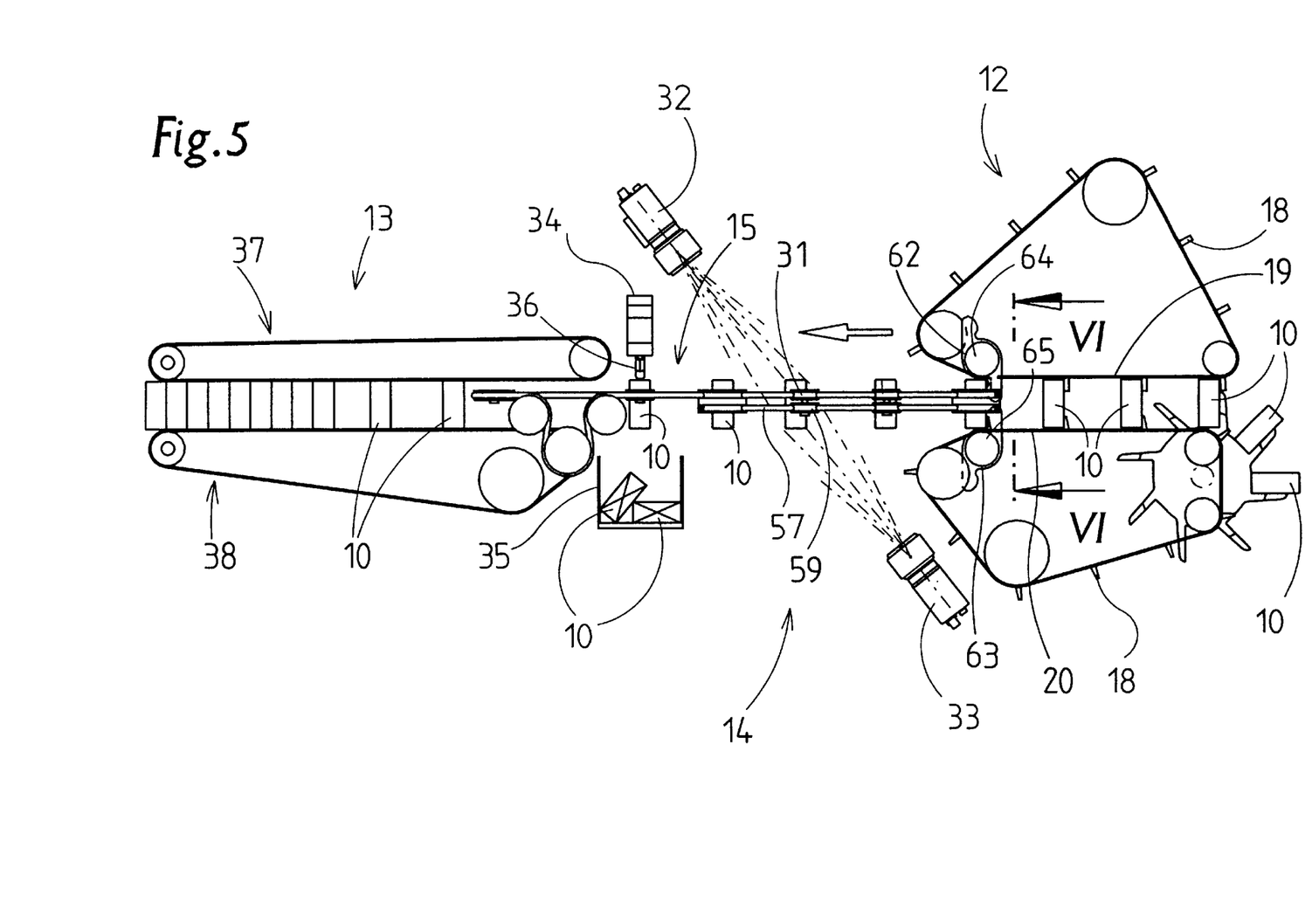
FIG. 5 shows a schematic side view of a further apparatus for checking (cigarette) packs.
Figure 6:
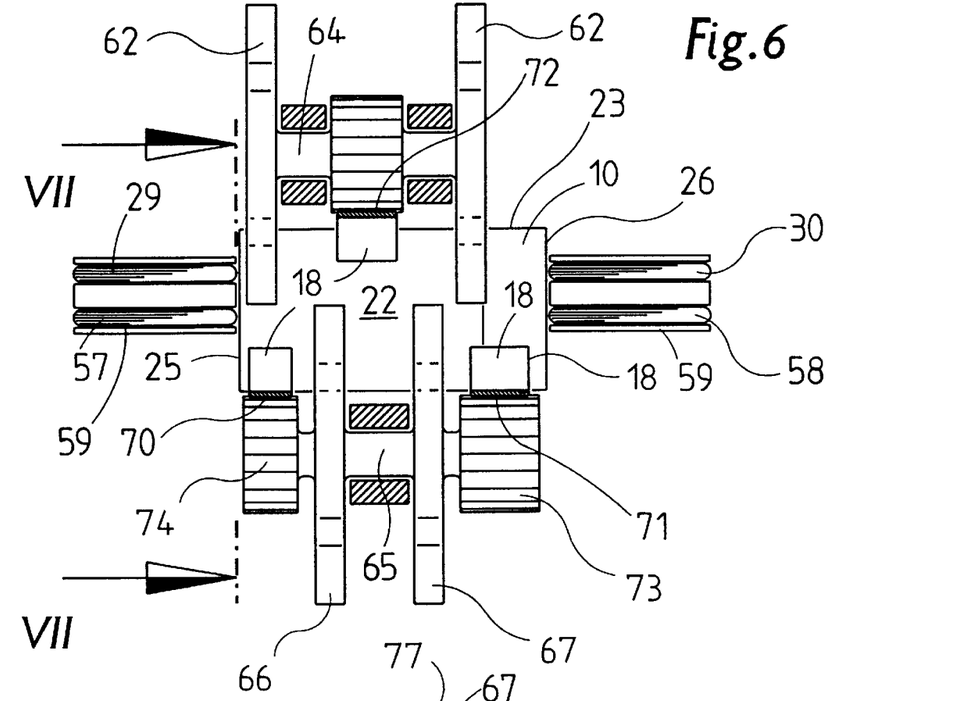
FIG. 6 shows, on an enlarged scale, a detailed schematic view of the transition between a feed conveyor and the checking section in the section plane VI—VI of FIG. 5.
Figure 7:
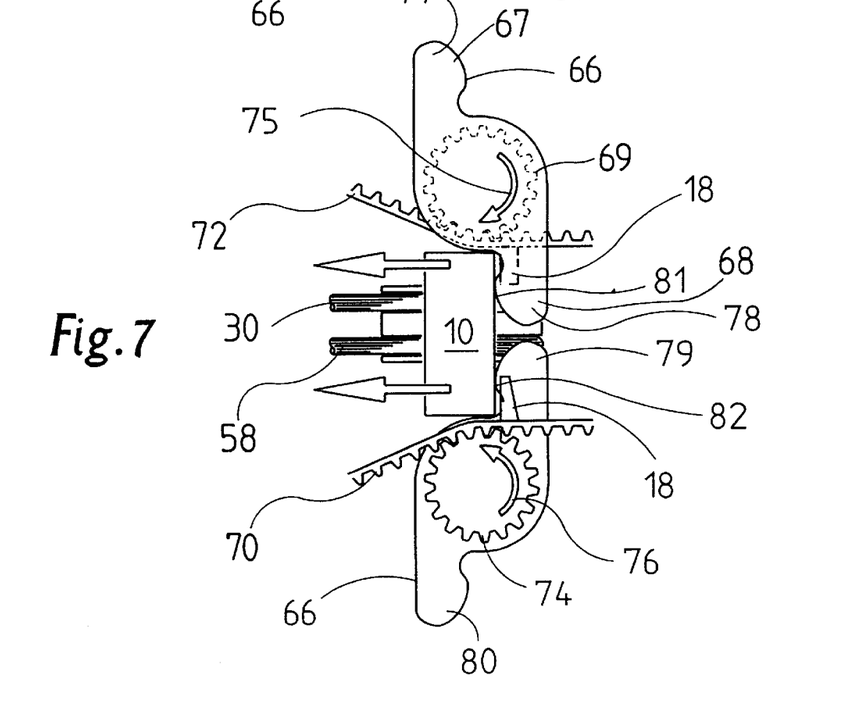
FIG. 7 shows a transverse view of the illustration according to FIG. 6 in the section plane VII—VII of FIG. 6.

FIG. 5, FIG. 6, and FIG. 7 show a further embodiment of a checking apparatus for (cigarette) packs 10.

A special feature of this embodiment is the configuration of the checking conveyor 15. As shown by the embodiment in FIG. 1, it comprises two lateral round bands 29, 30, which lie on the lateral end surfaces 25, 26 of the packs 10. In addition, arranged in a partial region of the checking section 14 or of the checking conveyor 15 below the round bands 29, 30 is an additional conveying means for gripping the packs 10. The additional conveyor also comprises round bands 57, 58, which run in parallel fashion below the round bands 29, 29 and at a distance to same. The round bands 57, 58 are also led through supporting rollers 59, which are positioned equiaxial below the supporting rollers 31.

The aforementioned, additional endless conveyor for the packs, i.e. round bands 57, 58 extends from the feed conveyor 12, along its own checking section 14, ending however at a distance from the ejector 34. The latter is accordingly operative in a region in which the packs 10 are exclusively conveyed by the (upper) round bands 29, 30.

A further special feature has been realized for the transfer of packs 10 from feed conveyor 12 to the checking conveyor 15. In the exemplary embodiment, the checking conveyors, namely the round bands 29, 30 and the round bands 57, 58, end in the region of deflector rollers 60, 61 of the conveying strands 19, 20 of the feed conveyor 12. To ensure a reliable and above all a precisely-positioned transfer of the packs 10 from the feed conveyor 12 to the checking conveyor 15, special transfer means are positioned in the region of the deflector rollers 60, 61. They are designed so that they can grip the packs 10 in the region of the pack rear side 22 and transfer them with accelerated movement to the region of the round bands 29, 30; 57, 58.

These transfer means are rotary-driven vaned wheels 62, 63, which are arranged in the region of the conveying strands 19, 20, specifically equiaxial to the deflector rollers 60, 61. The vaned wheels 62, 63 are driven at a speed synchronized with the feed conveyor 12. To achieve this purpose, the vaned wheels 62, 63 are connected to the deflector rollers 60, 61. The latter themselves are configured as toothed wheels. Accordingly, the conveying strands 19, 20 comprise toothed belts which mesh with the teeth of the deflector rollers 60, 61.

As shown in FIG. 6, provided above and below the movement path of the packs 10, namely in the region of the conveying strands 19 and 20, are vaned wheels 62, 63, with two vaned wheels mounted in each case on a common axle or shaft 64, 65. The upper vaned wheels 62 are arranged at a significant distance from one another, thus gripping the packs at a region adjacent to the end surfaces 25, 26 of the rear side 22. The lower vaned wheels 63 are spaced at a lesser distance to one another and grip the packs 10 at a central region of the rear side 22.

The vaned wheels 62, 63 have been given a special configuration. Each vaned wheel 62, 63 comprises a plurality, namely two nearly diametrically opposed vanes 66, 67. When the vaned wheels 62, 63 rotate, said vanes move from the top to the bottom against the rear side 22 of the packs. The side of the vanes 66, 67 facing the packs 10 has an S-shaped configuration with a crown-like projection 68. The latter comes to rest on the rear side 22.

To ensure a precise, upright position of the packs 10, they are adjustably gripped in the region of their vertically-directed side surfaces 23, 24. For this purpose, the vaned wheels 62, 63 have a circular-shaped middle part 69. Vanes 66, 67 are connected to the middle section 69 in an offset manner relative to the revolving axis of the vane wheels 62, 63. A portion of the (circular) circumferential surface of the middle part 69 lies on the upper and lower side surfaces 23, 24 of the checking conveyor 15 when the packs 10 are transferred (FIG. 7).

Another special feature is the design of the feed conveyor 12 in this exemplary embodiment. As can be seen in FIG. 6, the bottom belt 17 comprises two single belts 70, 71 lying at a distance from one another. The latter are configured as having different widths in order to ensure optimum guidance of various sized packs 10. The lower vaned wheels 63 are arranged between the two deflector rollers 61 assigned to the single belts 70, 71.

The top belt 16 comprises a single belt 72, which runs centered or slightly offset to the middle of the packs and single belts 70, 71. Single belt 72 is led over a single deflector roller 60. The two vaned wheels 62 are arranged on both sides of the single belt 72.

LIST OF DESIGNATIONS

10 pack
11 conveying section
12 feed conveyor per second
13 removal conveyor
14 checking section
15 checking conveyor
16 top belt
17 bottom belt
18 carry-along element
19 conveying strand sensor
20 conveying strand
21 front side
22 rear side
23 side surface
24 side surface
25 end surface
26 end surface
27 star wheel
28 carry-along element
29 round band
30 round band
31 supporting roller
32 camera
33 camera
34 ejector
35 collecting container
36 push rod
37 conveying belt
38 conveying belt
39 activating sensor
40 mirror
41 light beam
42 defect sensor
43 spacing
44 spacing
45 evaluation window
46 angular encoder
47 spacing
48 measured value of pulses
49 reaction time
50 multiplier
51 correction value
52 parameter
53 subtraction
54 signal of the defect
55 signal for ejector
56 ejection
57 round band
58 round band
59 supporting roller
60 deflector roller
61 deflector roller
62 vaned wheel
63 vaned wheel
64 shaft
65 shaft
66 vane
67 vane
68 projection
69 middle part
70 single belt
71 single belt
72 single belt

What is claimed is:

1. An apparatus for checking packs (10) for a correct configuration of their outer appearance, wherein the packs are transported in a downstream direction by a checking conveyor (15) in a region of a checking section (14) at a spacing from one another, wherein, positioned in the region of the checking section (14) are optoelectronic checking means (32, 33) for registering the outer appearance of a pack (10), and, wherein in the case of a defective pack (10), an ejector (34), located downstream of the checking means, is actuated for discharging the defective pack (10), said apparatus comprising:

an activating sensor (39) in the region of the checking section (14) and located upstream of the checking means (32, 33), wherein the activating sensor (39) is activated by a pack (10) moved past the sensor and directly switches on the checking means (32, 33);

located upstream of the checking conveyor (15), a feed conveyor (12) having a conveying speed and having conveying strands (19, 20) lying respectively on top and bottom side surfaces (23, 24) of the packs (10), wherein the packs (10) are transported by the feed conveyor (12) into an initial region of the checking conveyor (15) and are transferred thereto and a transfer conveyor, arranged in the region of transfer from the feed conveyor (12) to the checking conveyor (15), for gripping each pack (10) on a rear side (22) thereof for a precisely positioned introduction of the packs (10) into the checking conveyor (15), wherein the transfer conveyor comprises vaned wheels (62, 63) which run synchronously with the feed conveyor (12), gripping each pack (10) with a vane (66, 67) simultaneously from above and from below.

2. The apparatus according to claim 1, wherein the vaned wheels (62, 63) grip the rear side (22) of each pack (10) with a crown-like projection (68) and guide vertically oriented surfaces of the pack (10).

3. The apparatus according to claim 1, wherein the vaned wheels comprise vanes (66, 67), and wherein the packs (10) are driven by the vanes (66, 67) into a region of the feed conveyor (12) at a conveying speed that is greater than the conveying speed of the feed conveyor (12).

4. A method of checking packs (10) from a packaging machine for a collect configuration of their outer appearance, wherein the packs (10) are transported in a downstream direction along a conveying path by a conveyor along a checking section (14) and are moved past stationary checking means, wherein defective packs (10) are sorted out downstream of the checking means, wherein the checking means is activated cyclically for scanning a pack (10) as each pack is moved past the checking means, wherein the checking means is switched on by an activating sensor (39) which is, activated by the pack (10) to be checked, wherein a defective pack (10) is sorted out of the conveying path of the packs (10) by an ejector (34) which is actuated by a defect sensor (42) which, in turn, is activated by the defective pack (10) moved past the defect sensor (42), said method further comprising the step of actuating the ejector (34) with a time delay which varies in dependence on an operating speed of the packaging machine.

5. The method according to claim 4, further comprising the step of changing the time delay in accordance with an angular encoder (46) in a region of a preliminary conveyor which feeds the packs (10).

6. The method according to claim 5, further comprising the steps of:

maintaining the defect sensor (42) active at all times so that all the packs (10) conveyed past the sensor are scanned for determining a correct, predetermined spacing between the packs (10); and in the case of a defective pack (10), causing the ejector (34) to receive a signal from the checking means such that the ejector (34) becomes active when the defective pack (10) is moved past the defect sensor (42).

7. The method according to claim 5, further comprising the step of operating the defect sensor (42) with an evaluation window (45) such that defective packs, which enter into a region of action of the defect sensor (42) within a predetermined spacing or a predetermined time span, are scanned.

8. The method according to claim 7, further comprising the step of varying the evaluation window (45) of the defect sensor (42) in dependence on the operating speed of the packaging machine.

9. An apparatus for checking packs (10) from a packaging machine for correct configuration of their outer appearance, wherein the packs are transported in a downstream direction at a conveying speed along a conveying path by a checking conveyor (15) in a region of a checking section (14) and at a spacing from one another; wherein there are positioned in the region of the checking section (14) optoelectronic checking means for scanning the outer appearance of a pack (10), wherein, in the case of a defective pack (10), an ejector (34) located downstream of the checking means is actuated for discharging the defective pack (10), wherein an activating sensor (39) in a region of the checking section (14) is located upstream of the checking means, wherein the activating sensor (39) is activated by a passing pack (10) and the checking means is directly switched on immediately, wherein the defective pack (10) is sorted out of the conveying path of the packs (10) by an ejector (34), and wherein the ejector (34) is actuated by a defect sensor (42) which is activated by a passing defective pack (10), said apparatus further comprising means for activating the ejector (34) with a time delay which varies in dependence on an operating speed of the packaging machine.

10. The apparatus according to claim 9, wherein the packs (10) in the region of the checking section (14) are transported by two mutually opposed endless conveyors, serving as checking conveyors (15), which lie against laterally directed surfaces of the packs.

11. The apparatus according to claim 10, wherein, at least in a first partial region of the checking section, the endless conveyors for the packs (10) comprise a plurality conveyors or round bands (20, 30; 60, 61) which are arranged one above the other and which lie on the laterally directed pack surfaces.

12. The apparatus according to claim 11, wherein the packs (10) in a region of the ejector (34) are conveyed only by two mutually opposed endless conveyors.

13. The apparatus according to claim 9, wherein, arranged upstream of the checking conveyor (15) is a feed conveyor (12) with conveying strands (19, 20) running above and below the conveying path of the packs (10) and lying respectively on top and bottom side surfaces (23, 24) of the packs (10), and wherein the packs (10) are transported by the feed conveyor (12) into an initial region of the checking conveyor (15) and transferred thereto, said apparatus further comprising a transfer conveyor, arranged in a region of the transfer from the feed conveyor (12) to the checking conveyor (15), for gripping each pack (10) on a rear side (22) thereof for a precisely positioned introduction of the packs (10) into the checking conveyor (15).

14. The apparatus according to claim 13, wherein the transfer conveyor comprises two upper and two lower vaned wheels (62, 63) which grip in pair-like fashion the rear side (22) of each pack (10), wherein the vaned wheels (62, 63) run synchronously with the feed conveyor (12), gripping in each pack (10) with vanes (66, 67) simultaneously from above and from below.

15. The apparatus according to claim 14, wherein the vaned wheels (62, 63) grip the rear side (22) of each pack (10-) with a crown-like projection (68) and guide vertically oriented surfaces of the pack (10) with a transverse, circular-shaped middle part (69).

16. The apparatus according to claim 14, wherein the vanes (66, 67) introduce the packs (10) into a region of the feed conveyor (12) at a conveying speed which is greater than a conveying speed of the feed conveyor (12).

* * * * *